(12) United States Patent
Assmann et al.

(10) Patent No.: US 8,977,341 B2
(45) Date of Patent: Mar. 10, 2015

(54) MEASURING DEVICE AND A MAGNETIC RESONANCE DEVICE WITH THE MEASURING DEVICE

(75) Inventors: Bernd Assmann, Fürth (DE); Michael Frank, Erlangen (DE); Sven Heggen, Erlangen (DE); Ernst Mustafa, Fürth (DE); Jürgen Rössler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/449,722

(22) Filed: Apr. 18, 2012

(65) Prior Publication Data

US 2012/0271154 A1 Oct. 25, 2012

(30) Foreign Application Priority Data

Apr. 21, 2011 (DE) .................. 10 2011 007 859

(51) Int. Cl.
*A61B 5/055* (2006.01)
*A61B 7/00* (2006.01)
*G01R 33/567* (2006.01)
*A61B 5/00* (2006.01)

(52) U.S. Cl.
CPC . *A61B 7/00* (2013.01); *A61B 5/055* (2013.01); *G01R 33/5673* (2013.01); *A61B 5/7285* (2013.01); *A61B 2562/0204* (2013.01); *A61B 2562/223* (2013.01)
USPC ........... 600/413; 600/407; 600/410; 600/425; 600/428

(58) Field of Classification Search
USPC ................. 600/407, 410, 418, 425, 428, 413
See application file for complete search history.

(56) References Cited

U.S. PATENT DOCUMENTS

| | | | |
|---|---|---|---|
| 3,682,161 A * | 8/1972 | Alibert | 600/500 |
| 4,819,753 A | 4/1989 | Higo et al. | |
| 5,022,405 A * | 6/1991 | Hok et al. | 600/528 |
| 6,771,999 B2 * | 8/2004 | Salla et al. | 600/413 |
| 2003/0036693 A1 * | 2/2003 | Avinash et al. | 600/413 |

FOREIGN PATENT DOCUMENTS

| | | |
|---|---|---|
| DE | 1806623 A1 | 5/1970 |
| DE | 1303534 B | 2/1972 |
| DE | 3645212 C2 | 11/1995 |
| DE | 102009034054 A1 | 8/2010 |
| JP | 2007082914 A | 4/2007 |
| WO | WO 2008077495 A1 | 7/2008 |

OTHER PUBLICATIONS

Niendorf Thoralf, et al.; High-field cardiovascular MRI makes sustained progress, in: Diagnostic Imaging Europe, 2009, pp. 1, 11, 12, 14, 16, 17; Others; 2009.

(Continued)

*Primary Examiner* — Peter Luong

(57) ABSTRACT

A measuring device for a magnetic resonance device is provided. The measuring device has a sensor unit. The sensor unit includes at least one acoustic sensor element for detecting heart sounds of a patient. The sensor unit also includes a resonating body unit. The resonating body unit has a hollow space for filtering interfering signals emitted by the magnetic resonance device from the heart sounds of the patient.

14 Claims, 3 Drawing Sheets

(56) References Cited

OTHER PUBLICATIONS

Maderwald S., et.al.: "Tesla Cardiac Imaging with a Phonocadiogram Trigger Device", at: 19th Annual Meeting and Exhibition ISMRM 2011, Montreal, Canada, May 2011, pp. 41; Others; 2011.

Frauenrath Tobias, et.al.: "Acoustic Method for Synchronization of Magnetic Resonance Imaging (MRI)", in: Acta Acustica United with Acustica, 2008, vol. 94, No. 1, pp. 148-155; Others; 2008.

Frauenrath T., et.al.: Feasibility of Cardiac Gating Free of Interference With Electro-Magnetic Fields at 1.5 Tesla, 3.0 Tesla and 7.0 Tesla Using an MR-Stethoscope, in: Investigative Radiology, Sep. 2009, vol. 44, No. 9, pp. S1-S9; Others; 2009.

Becker Meike, et al. Companson of Left Ventricular Function Assessment Using Phonocardiogram and Electrocardiogram Triggered 2D SSFP CINE MR Imaging at 1.5 T and 3 0 T, in European Radiology, Editonal Office Neutorgasse 9/2a, 1010 Vienna Austria, pp. 1-24, Book, Epub Dec. 16, 2009.

* cited by examiner

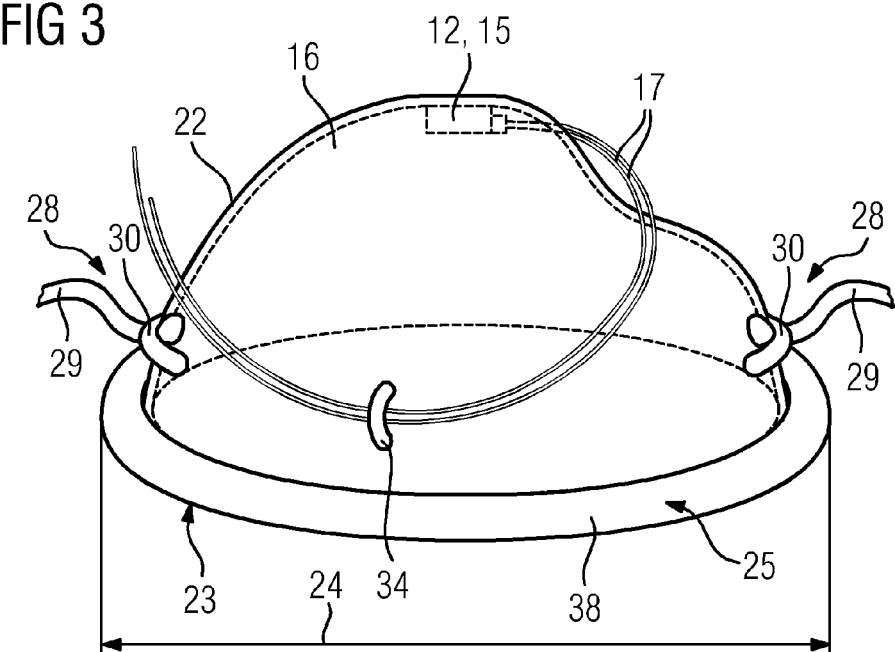
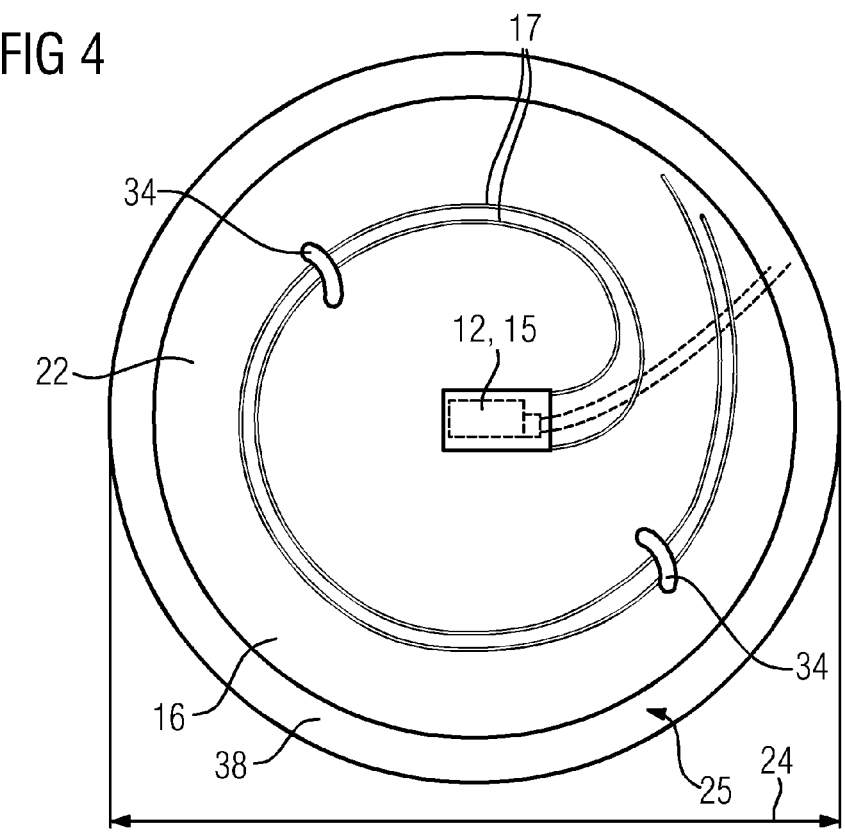

MEASURING DEVICE AND A MAGNETIC RESONANCE DEVICE WITH THE MEASURING DEVICE

CROSS REFERENCE TO RELATED APPLICATIONS

This application claims priority of German application No. 10 2011 007 859.2 filed Apr. 21, 2011, which is incorporated by reference herein in its entirety.

FIELD OF INVENTION

The present invention relates to a measuring device having a sensor unit comprising at least one acoustic sensor element for detecting heart sounds of a patient.

BACKGROUND OF INVENTION

In order to provide cardiac imaging for a patient, an imaging device, such as a magnetic resonance device in particular, must be synchronized with a heart signal of the patient. Arranging EKG electrodes on the chest of a patient, the electrodes being wired for a signal transmission, is known by way of example for this purpose.

It is furthermore known to use a microphone for capturing heart signals. However, this has the disadvantage that background noises, such as for example the loud noise from the magnetic resonance imaging, overlie the heart signal, especially heart sounds. This can lead to an interference in synchronization and therefore an associated degradation in image quality of the magnetic resonance imaging.

SUMMARY OF INVENTION

The object underlying the invention is in particular to provide a measuring device which contributes to a reduction of interfering signals during the capturing of heart sounds. The object is achieved through the features of the independent claims. Advantageous embodiments are described in dependent claims.

The invention relates to a measuring device having a sensor unit comprising at least one acoustic sensor element for detecting heart sounds of a patient.

It is proposed that the sensor unit has a resonating body unit comprising a hollow space, through which an advantageous capture, in particular an advantageous acoustic capture, of heart sounds can be achieved. In this connection, undesired interfering sounds, for example interfering sounds and/or knocking sounds which are emitted by a magnetic resonance device are at least reduced and/or suppressed within the hollow space of the resonating body unit and in such a way that the heart sounds are filtered out from the interfering signals and conducted to the at least one acoustic sensor element. The resonating body unit comprising the hollow space is preferably arranged upstream of the at least one acoustic sensor along a signal path of the heart sounds which are to be detected. In a particularly advantageous manner, the at least one acoustic sensor element is arranged on the resonating body unit so that the at least one acoustic sensor element lies directly on the patient by means of the resonating body unit.

The signal of the heart sounds of a patient to be detected by the inventive measuring device can be used with a heartbeat of the patient for synchronization of a medical imaging device, in particular a magnetic resonance device, so that precise timing of medical imaging with the heart frequency can be achieved.

In a particularly advantageous manner, the resonating body unit has a form which acts as a frequency filter and/or a frequency-dependent acoustic wave conductor up to a maximum frequency of approx. 80 Hz, whereby an advantageous separation of the heart sounds from the interfering signals within the resonating body unit can result. The form of the resonating body unit is thereby advantageously adapted to acoustic frequencies of the human heart, which generally lie in the range of at least a few Hz up to approx. 80 Hz. In such a manner, the acoustic heart sounds up to a maximum frequency of approx. 80 Hz can be conducted within the resonating body unit to the at least one acoustic sensor element, for example an optical microphone, and captured there due to the form of the resonating body unit. On the other hand interfering signals with a frequency of over 80 Hz are suppressed due to the form of the resonating body unit. In this context, below a maximum frequency of approx. 80 Hz is particular to be understood as a maximum frequency which is preferably arranged within a range of ±20 Hz around the frequency of 80 Hz and particularly preferably arranged within a range of ±10 Hz around the frequency of 80 Hz.

The resonating body unit here can be at least partially bell-shaped or helical, since both these forms are particularly advantageously suited to suppressing the undesired interfering noise with a frequency of more than approx. 80 Hz. Additionally, by means of the two forms, only the heart sounds and/or acoustic heart signals up to a maximum frequency of approx. 80 Hz can be conducted to the at least one acoustic sensor element. The resonating body unit here is embodied such that an entire heart region of a chest area of the patient is covered by the resonating body unit and the most effective possible capturing of the acoustic heart signals is therefore achieved.

It is furthermore proposed that resonating body unit has an open side opening out onto a support plate on a patient. The resonating body unit having the open side advantageously sits on one of the chest areas of the patient covering the heart. An acoustic heart signal, in particular a heart sound or heart noise can advantageously reach the hollow space of the resonating body unit and there be filtered out from the interfering signals and/or interfering noises due to the form of the resonating body unit, and be relayed.

In an advantageous embodiment of the invention, it is proposed that the sensor unit on the open side has a sealing unit which frames the resonating body unit on the open side. An improved positioning of the resonating body unit, in particular one which involves it nestling against the patient, and additionally an advantageous screening of undesired interfering noises can be achieved. The sealing unit also contributes in this situation to the conducting of the acoustic heart sounds into the hollow space of the resonating body unit.

If the sealing unit is made of an elastic material, an advantageous positioning of the resonating body unit on the patient can be achieved, which can also smooth out the unevenness of a body surface of the patient. The elastic material of the sealing unit can be made by way of example from an elastic rubber material and/or an elastic silicone material and/or an elastic plastic material and/or another elastic material which appears expedient to the person skilled in the art. Here, "body surface of the patient" is understood to be the bare skin of the patient and/or a surface of an item of clothing which the patient may still have on (e.g. an undershirt).

It is further proposed that the sealing unit has a hollow space and an elastic filling element, the elastic filling element being arranged within the hollow space. This enables the resonating body unit to be adjusted in a particularly flexible manner when it is positioned on a chest area of the patient and/or a high damping capacity for interfering noises to be advantageously achieved. The elastic filling element can be made from a gas and/or a foam and/or a gel and/or a liquid and/or another elastic material which appears expedient to the person skilled in the art. An elastic filling element here is in particular understood to be a filling element which can change its shape due to the action of the force of gravity of the resonating body unit such that a complete, ring-shaped positioning contact of the sealing unit can be achieved on a body area of the patient and such that intermediate spaces which can lead to an undesired infiltration of interfering signals and/or interfering noises into the hollow space of the resonating body unit and/or can lead to the acoustic heart sounds leaking from the hollow space of the resonating body unit between the body of the patient and the sealing unit can be prevented.

It is further proposed that the sensor unit comprise at least one damping element which is at least partially arranged on an outer surface of the resonating body unit. In particular an infiltration of interfering noises and/or interfering signals through the outer wall of the resonating body unit can be reduced and/or prevented. The damping element is preferably formed by a damping layer which is arranged on the outer surface of the resonating body unit. The damping layer can be made by way of example of a layer made of a foam material and/or of other damping layers which appear expedient to the person skilled in the art for the purpose of damping interfering noises within the hollow space of the resonating body unit.

It is additionally proposed that the sensor unit has at least one fixing unit for the purpose of fixing the resonating body unit onto the patient. A secure positioning of the sensor unit on the patient so that it is unable to slip out of place is able to be achieved for detecting the heart sounds. The fixing unit can be formed by way of example by a fixing belt, which can additionally be embodied as an elastic belt.

In a further embodiment of the invention, it is proposed that the at least one acoustic sensor element is formed at least partially by an optical microphone. This allows the measuring device, in particular the sensor unit, to be particularly advantageously integrated into a measuring operation of a magnetic resonance device, since interference with the measuring operation of the magnetic resonance device is prevented due to the preferably metal-free embodiment of the optical microphone. In addition, the optical microphone can directly capture the heart sounds by means of the resonating body unit and a signal transmission between the resonating body unit and the optical microphone by means of a cabling connection can advantageously be avoided. An optical microphone in this context is understood to be a microphone in which light from a light source, by way of example a light-emitting diode is directed at a membrane, in particular a reflective membrane, wherein the membrane reflects at least a part of the light. The light is thereby conducted preferably by means of glass fiber cabling towards or away from the membrane. If the membrane moves due to acoustic waves, the reflected beam is offset in relation to the incident beam so that less light is able to be coupled into the glass fiber cabling for the purpose of conducting away the reflected light. An intensity of the reflected light can subsequently be used to infer a movement of the membrane, and the acoustic waves can thereby be captured. As an alternative, the optical microphone can also be embodied without membrane, with the effect being exploited here that a pulsed light beam can be modulated by sound in its frequency and/or amplitude. The acoustic waves in this case can be captured by capturing a change in the amplitude and/or the frequency of the pulsed light beam in relation to a reference beam.

It is further proposed that the resonating body unit has a holding unit for receiving the at least one acoustic sensor element and the holding unit is arranged on an end portion of the resonating body unit facing away from the open side. Preferably only the signals with a maximum frequency of up to approx. 80 Hz, in particular heart noises of the patient, can thereby reach the at least one acoustic sensor element and in such a way that a low-noise and low-interference capturing of the heart signals, in particular of heart noises, within the at least one acoustic sensor element can advantageously be achieved.

It is further proposed that the sensor unit comprise at least one holding element for the purpose of supporting at least one glass fiber cable of the sensor unit and the at least one holding element is arranged on the resonating body unit. The glass fiber cable can in this way particularly advantageously be protected from undesired damage, such as by way of example a fracturing or a kinking of the glass fiber cable, in that the glass fiber cable can remain connected to the acoustic element without strain due to the at least one holding element, such as for example during a re-positioning of the sensor unit and/or the patient. The at least one holding element is particularly advantageously arranged on an outer surface of the resonating body unit and/or on a damping layer arranged on the outer surface.

The at least one acoustic sensor element and/or the at least one glass fiber cable are particularly advantageously arranged in a removable manner on the resonating body unit, allowing the sensor unit to be mounted on the patient in a user-friendly manner. In this way, the at least one acoustic sensor element and/or the at least one glass fiber cable can be arranged on the resonating body unit after a positioning of the resonating body unit on the patient. In this context, "arranged in a removable manner" is taken to mean that the at least one acoustic sensor element and/or the at least one glass fiber cable still retain a fully operational capability of the at least one acoustic sensor element and/or the at least one glass fiber cable after they are removed or detached from the resonating body unit.

It is furthermore proposed that the sensor unit is embodied as magnetic resonance-compatible so that the sensor unit can be particularly advantageously implemented together with a magnetic resonance device for synchronized magnetic resonance imaging.

It is additionally proposed for the measuring device to have a postprocessing unit and a signal transmission unit for wireless signal transmission between the sensor unit and the postprocessing unit. This allows an advantageous separation between the sensor unit and the postprocessing unit to be achieved and in such a way for example that the postprocessing unit is arranged in a protected manner outside of an area subject to a magnetic field for a magnetic resonance measurement.

The invention further relates to a magnetic resonance device having a measuring device, wherein by means of the measuring device, a heart signal is captured for generating a trigger signal for magnetic resonance imaging.

BRIEF DESCRIPTION OF THE DRAWINGS

Further advantages, features and details of the invention are disclosed in the exemplary embodiments described below as well as with the aid of the drawings, in which:

FIG. 3 shows a second embodiment of a resonating body unit of the measuring device in a side view, FIG. 4 shows the second embodiment of a resonating body unit of the measuring device in a plan view.

DETAILED DESCRIPTION OF INVENTION

Figure 1:
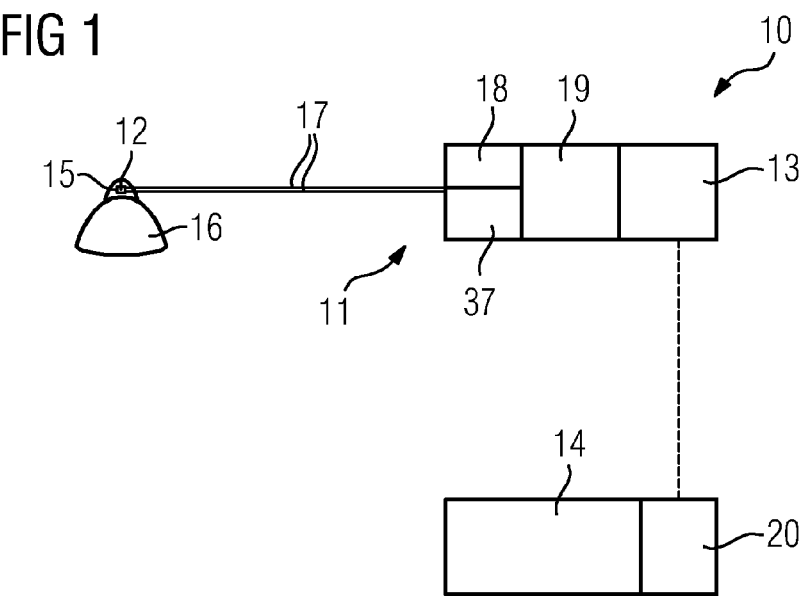
FIG. 1 shows a schematic illustration of an inventive measuring device.

FIG. 1 schematically illustrates an inventive measuring device 10. The measuring device 10 used to capture and/or detect heart signals and for this purpose has a sensor unit 11 comprising an acoustic sensor element 12. The measuring device 10 furthermore comprises a signal transmission unit 13 and a postprocessing unit 14. In an alternative embodiment, the sensor unit 11 can also comprise two or more acoustic sensor elements 12.

In the present exemplary embodiment, the acoustic sensor element 12 is formed by an optical microphone 15 and is provided for detecting heart sounds of a patient 104. To this end, the sensor unit 11 comprises a light-emitting diode 37 which generates a light beam which is conducted towards the optical microphone 15 via a glass fiber cable 17 and is reflected there. In an alternative embodiment of the invention, the acoustic sensor element 12 can also have a different construction to the optical microphone.

The sensor unit 11 comprises a resonating body unit 16 (FIGS. 1 to 5) which is positioned on a chest, in particular a heart area of the chest of a patient 104, to capture an acoustic heart signal and which conducts the heart sounds to the optical microphone 15. The optical microphone 15 captures the heart sounds as optical signals due to the reflection of the light beam incident at the optical microphone 15 via the glass fiber cable 17. These optical signals are conducted by means of a further glass fiber cable 17 to a signal converter unit 18 of the sensor unit 11 and are converted there into electrical signals. The signal converter unit 18 can comprise by way of example a photo diode and/or further units which appear expedient to the person skilled in the art.

The electrical signal subsequently passes through a signal filtering unit 19 of the sensor unit 11 and is conducted to the signal transmission unit 13. The signal transmission unit 13 is used for wirelessly transmitting signals between the sensor unit 11 and the postprocessing unit 14. To this end, the electrical signals are sent to the postprocessing unit 14 which has a signal receiving unit 20 for that purpose. The signals which are sent in this case can be digital or analog signals. The postprocessing unit 14 comprises a computing unit which processes the signals captured by the sensor unit using the corresponding software and/or the corresponding programs. Here, the signals are processed, inter alia, to generate a trigger signal for a medical imaging device, in particular a magnetic resonance device 100 (see FIG. 6) so that magnetic resonance imaging can be synchronized with the trigger signal for a magnetic resonance measurement.

As an alternative thereto, the measuring device 10 can also have a data cable for transmitting signals between the sensor unit 11 and the postprocessing unit 14.

Figure 2:
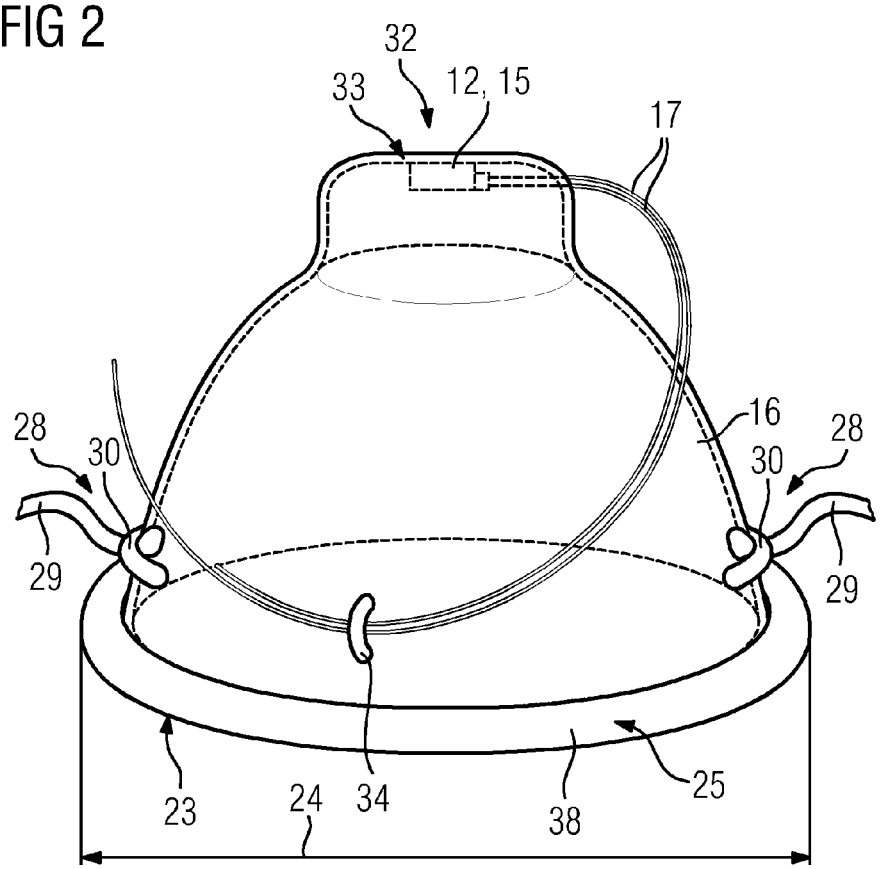
FIG. 2 shows a first embodiment of a resonating body unit of the measuring device in a side view.

In FIGS. 2 to 4, a partial area of the sensor unit 11 with the resonating body unit 16 is shown in more detail. The resonating body unit 16 is embodied as hood shaped and has a hollow space 36 in order to filter the noises infiltrating the resonating body unit 16 according to their frequency and preferably to selectively relay only the heart noises or heart sounds within the resonating body unit 16. The resonating body unit 14 hereby has a form which acts as a frequency filter and/or a frequency-dependent acoustic wave conductor up to a maximum frequency of approx. 80 Hz, so that predominantly the heart sounds or heart noises of the patient are relayed within the resonating body unit 16 and undesired interfering noises are filtered out due to the form of the resonating body unit 16. In the exemplary embodiment shown in FIG. 2, the resonating body unit 16 is bell-shaped 21. In the exemplary embodiment shown in FIGS. 3 and 4, the resonating body unit 16 is helical 22.

The two exemplary embodiments shown in FIGS. 2 to 4 only differ in respect of the form of the resonating body unit 16, so that the mode of operation and construction of the resonating body unit 16 described below relate equally to both exemplary embodiments.

The hood-shaped resonating body unit 16 in FIGS. 2 to 4 additionally has an open side 23 for positioning on the patient 104. The resonating body unit 16 is embodied such that the open side 23 covers an area of the patient 104 which completely covers the heart of the patient 104 and therefore enables the most effective possible capturing of the acoustic heart signals. The resonating body unit 16 has a diameter 24 of at least 10 cm and preferably of approx. 15 cm on the open side 23.

The sensor unit 11 further comprises a sealing unit 25 on the open side, which frames the resonating body unit 16 on the open side 23. The sealing unit 25 has a sealing element 38 which is made of an elastic material such as by way of example in the present exemplary embodiments a rubber beading. By means of the sealing element 38, an advantageous positioning of the resonating body unit 16 on the patient is achieved in that the sealing element 38 nestles against the body of the patient 104, in particular against the skin of the patient 104 and/or an item of clothing worn by the patient 104. In this way an infiltration of interfering noises or background noises, the operating noise of the magnetic resonance device 100 by way of example, is reduced and/or prevented so that that heart sounds are relayed with the least possible interference from interfering noises within the hollow space 36 of the resonating body unit 16.

As an alternative to the sealing element 38 being embodied as a rubber beading, the sealing element 38 can also be made of a silicone and/or a plastic material, etc. Alternatively or in addition to this, the sealing unit 25 can also comprise an absorbent surface facing in the direction of the patient 104 so that the resonating body unit 16 can adhere automatically to the patient 104 for capturing the heart sounds.

Figure 5:
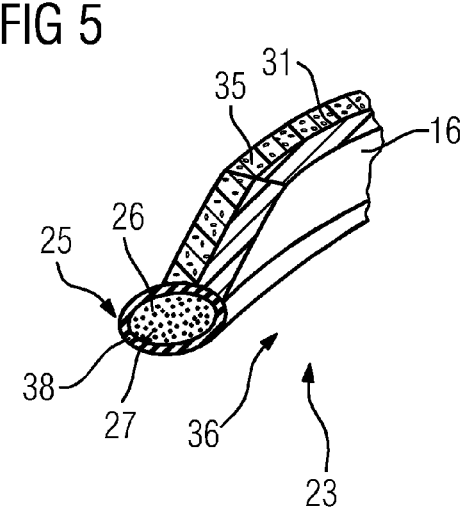
FIG. 5 shows a cross section through a sealing unit of the resonating body unit and FIG. 6 shows a schematic illustration of an inventive magnetic resonance device comprising the measuring device.

A section through the sealing unit 25 and a partial area of the resonating body unit 16 are illustrated in FIG. 5. The sealing unit 25 has a hollow space 26 which is surrounded in ring-shaped manner by the sealing element 38. An elastic filling element 27 is arranged in the hollow space 26 in order to allow an improved flexible and elastic nestling of the resonating body unit 16 against the patient 104. The elastic filling element 27 can be made from a gas, such as air for example, and/or a liquid and/or a gel and/or a foam and/or other elastic filling elements 27 which appear expedient to the person skilled in the art.

The sensor unit 11 further comprises a damping element 35 which is arranged on an outer surface 31 of the resonating body unit 16. The damping element 35 is made in the present exemplary embodiment (FIGS. 2 to 5) of a damping layer made of foam which is arranged on the outer surface 31 of the resonating body unit 16 and as such contributes to a screening of undesired interfering signals and/or undesired interfering noises.

The sensor unit 11 further comprises a fixing unit 28, by means of which the resonating body unit 16 is able to be fixed onto the patient 104, in particular onto the chest area of the patient 104, so that the resonating body unit 16 can be positioned on the patient 104 so that it is unable to slip out of place. The fixing unit 28 to this end comprises a fixing belt 29 which is fixed by means of holding elements 30 to the opposing areas of an outer surface 31 of the resonating body unit 16 and/or on the damping element 35.

A holding unit 33 of the resonating body unit 16 is arranged on an end portion 32 facing away from the open side 23. The holding unit 33 is used for receiving the optical microphone 15 so that the optical microphone 15 rests directly on the patient 104 together with the resonating body unit 16 to detect heart sounds. The holding unit 33 is embodied such that the optical microphone 15 is positioned removably in the holding unit 33. The optical microphone 15 by way of example can be taken out of the holding unit 33 to allow the positioning of the resonating body unit 16 on the patient 104 and can be replaced in the holding unit 33 following the positioning of the resonating body unit 16.

The optical microphone 15 is connected to the signal converter unit 18 for the purpose of signal transmission by glass fiber cabling 17. The sensor unit 11 comprises holding elements 34 which are arranged on the outer surface 31 of the resonating body unit 16 and/or on the damping element 35 for the purpose of routing the glass fiber cables 17 on the resonating body unit 16. The glass fiber cables 17 are supported between the outer surface 31 of the resonating body unit 16 and/or the damping element 35 and said holding elements 34. The glass fiber cables 17 are hereby supported without strain so that impairment and/or damage, such as a fracture or kinking of the glass fiber cables 17, is prevented, especially during positioning of the resonating body unit 16.

The glass fiber cables 17 are also stored in a removable manner in the holding elements 34 so that the glass fiber cables 17 together with the optical microphone 15 can be removed from the holding unit 33 and the holding elements 34 to allow positioning of the resonating body unit 16 on the patient 104, and following the positioning of the resonating body unit 16, can again be arranged in the holding unit 33 and the holding elements 34. In addition, the glass fiber cables 17 can also be arranged in a removable manner on the optical microphone 15, so that the optical microphone 15 or the glass fiber cables 17 can be removed from the holding unit 33 and the holding elements 34 independently of one other.

Figure 6:
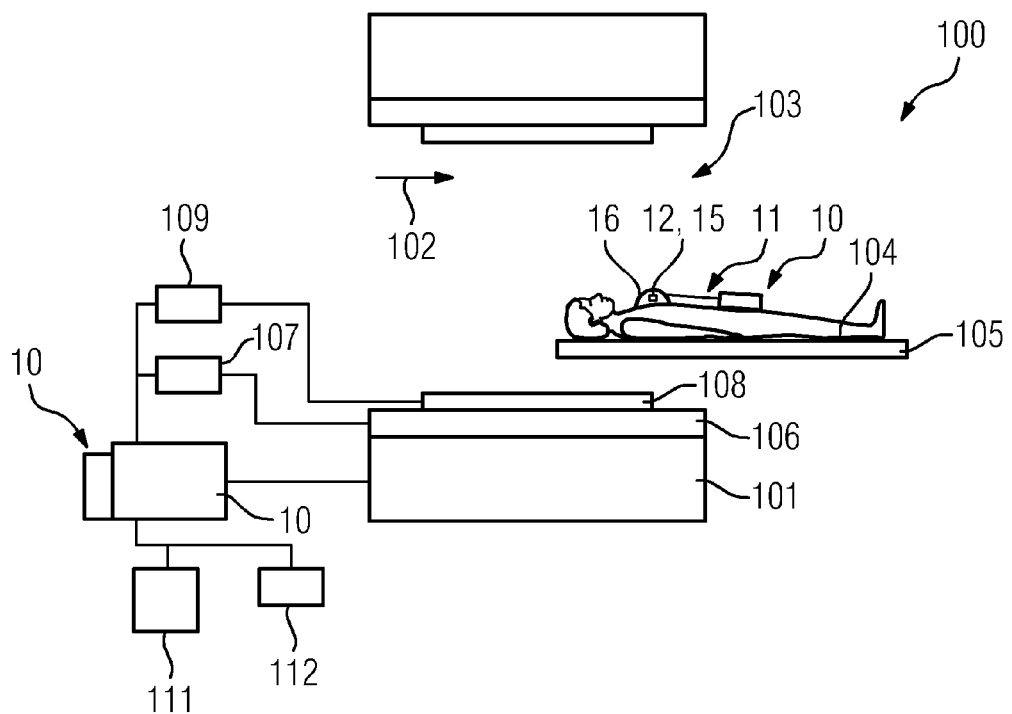

An inventive magnetic resonance device 100 is illustrated in FIG. 6. The magnetic resonance device 100 comprises a main magnet 101 for generating a strong and particularly a constant main magnetic field 102. In addition, the magnetic resonance device 100 comprises a cylinder-shaped receiving area 103 for receiving a patient 104, the receiving area 103 being surrounded in a circumferential direction by the main magnet 101. The patient 104 can be pushed into the receiving area 103 by means of a patient couch 105 of the magnetic resonance device 100.

The magnetic resonance device 100 furthermore has a gradient coil 106 for generating magnetic field gradients which are used for location coding during imaging. The gradient coil 106 is controlled by means of a gradient control unit 107. The magnetic resonance device 100 furthermore comprises high frequency antennas 108 and a high frequency antenna unit 109 for exciting a polarization which is established in the main magnetic field 102 generated by the main magnet 101. The high frequency antennas 108 are controlled by the high frequency antenna unit 109 and beam high frequency magnetic resonance sequences into an examination room which is essentially formed by the receiving area 103. In this way the magnetization is deflected from its state of equilibrium. In addition to this, magnetic resonance signals are received by means of the high frequency antenna unit 109.

The magnetic resonance device 100 comprises a control unit 110 for the purpose of controlling the main magnet 101, the gradient control unit 107 and for controlling the high frequency antenna unit 109. The control unit 110 centrally controls the magnetic resonance device 100, such as for example the carrying out of a predetermined imaging gradient echo sequence. Control information such as for example imaging parameters as well as reconstructed magnetic resonance images can be shown on a display unit 111 of the magnetic resonance device 100. The magnetic resonance device 100 additionally comprises an input unit 112, via which information and/or parameters can be input by an operator during a measuring procedure.

The magnetic resonance device 100 shown can naturally comprise further components conventionally contained in magnetic resonance devices 100. The general mode of operation of a magnetic resonance device 100 is additionally known to the person skilled in the art, so there is no need for a detailed description of the general components here.

The magnetic resonance device 100 further comprises the measuring device 10 as illustrated in more detail in FIGS. 1 to 5. A synchronization between the magnetic resonance device 100 and the heartbeat of the patient 104 takes place by means of the signal of the heart sounds captured and/or detected by the measuring device 100, so that there is precise timing of medical imaging with the heart frequency for magnetic resonance imaging. The sensor unit 11 of the measuring device 10 is embodied as magnetic resonance-compatible for a measuring operation of the magnetic resonance device 100 together with the measuring device 10.

The postprocessing unit 14 of the measuring device 10 is connected to the control unit 110 of the magnetic resonance device 100 via a data exchange unit. Alternatively, it is also possible for the postprocessing unit 14 of the measuring device 10 to be integrated in the control unit 110 of the magnetic resonance device 100. The postprocessing unit 14 of the measuring device 10 is arranged outside of the receiving area 103 and also outside of an area subject to the main magnetic field 12.

The invention claimed is:

1. A measuring device, comprising:
    a hood shaped resonating body comprising a hollow space configured to capture heart sounds of a patient and filtering interfering acoustic signals from the heart sounds of the patient; and
    an optical microphone configured to detect the filtered heart sounds of the patient conducted from the hood shaped resonating body,
    wherein the hood shaped resonating body has a shape configured as a frequency filter and a frequency-dependent acoustic wave conductor up to a maximum frequency of approximately 80 Hz.

2. The measuring device as claimed in claim 1, wherein the hood shaped resonating body is at least partially bell-shaped.

3. The measuring device as claimed in claim 1, wherein the hood shaped resonating body is at least partially helical.

4. The measuring device as claimed in claim 1, wherein the hood shaped resonating body comprises an open side for positioning the patient.

5. The measuring device as claimed in claim 4, further comprising an elastic beading that frames the hood shaped resonating body on the open side.

6. The measuring device as claimed in claim 5, wherein the elastic beading is made of a rubber, a silicone, or a plastic material and is ring-shaped.

7. The measuring device as claimed in claim 5, wherein the elastic beading surrounds a hollow space being filled by an elastic filling material.

8. The measuring device as claimed in claim 4, wherein the optical microphone is removably arranged on an end portion of the hood shaped resonating body facing away from the open side.

9. The measuring device as claimed in claim 1, further comprising a damping layer made of a foam material and arranged at least partially on an outer surface of the hood shaped resonating body.

10. The measuring device as claimed in claim 1, further comprising a fixing belt for fixing the hood shaped resonating body on the patient.

11. The measuring device as claimed in claim 1, further comprising a glass fiber cable connected to the optical microphone.

12. The measuring device as claimed in claim 1, wherein the measuring device is magnetic resonance-compatible.

13. The measuring device as claimed in claim 1, further comprising:
a computer for processing a signal captured by the optical microphone and
wherein the signal is wirelessly transmitted between the optical microphone and the computer.

14. A magnetic resonance device, comprising:
a magnet configured to generate a magnetic field;
a patient couch configured to push a patient into a cylindrical receiving area within the magnetic field; and
a measuring device configured to generate a trigger signal for magnetic resonance imaging, wherein the measuring device comprises:
a hood shaped resonating body comprising a hollow space configured to capture heart sounds of the patient and filtering interfering acoustic signals from the heart sounds of the patient; and
an optical microphone configured to detect the filtered heart sounds of the patient conducted from the hood shaped resonating body,
wherein the hood shaped resonating body has a shape configured as a frequency filter and a frequency-dependent acoustic wave conductor up to a maximum frequency of approximately 80 Hz.

* * * * *